(12) United States Patent
Van den Heuvel (10) Patent No.: US 9,849,284 B2
(45) Date of Patent: Dec. 26, 2017

(54) IMPLANTED AUDITORY PROSTHESIS CONTROL BY COMPONENT MOVEMENT

(71) Applicant: Koen Erik Van den Heuvel, Macquarie University (AU)

(72) Inventor: Koen Erik Van den Heuvel, Macquarie University (AU)

(73) Assignee: COCHLEAR LIMITED, Macquarie University (AU)

( * ) Notice: Subject to any disclaimer, the term of this patent is extended or adjusted under 35 U.S.C. 154(b) by 0 days.

(21) Appl. No.: 14/991,776

(22) Filed: Jan. 8, 2016

(65) Prior Publication Data
US 2016/0199644 A1 Jul. 14, 2016

Related U.S. Application Data
(60) Provisional application No. 62/101,080, filed on Jan. 8, 2015.

(51) Int. Cl.
*A61N 1/36* (2006.01)
*A61N 1/05* (2006.01)

(52) U.S. Cl.
CPC ....... *A61N 1/36032* (2013.01); *A61N 1/0541* (2013.01); *A61N 1/36036* (2017.08)

(58) Field of Classification Search
CPC .............. A61N 1/0541; A61N 1/36032; A61N 1/36128
USPC ...................................................... 607/57, 60
See application file for complete search history.

(56) References Cited

U.S. PATENT DOCUMENTS

| 7,561,708 | B2 | 7/2009 | Rohrlein |
| 2003/0050676 | A1* | 3/2003 | Hubelbank ........ A61N 1/37217 607/60 |
| 2005/0033383 | A1* | 2/2005 | Ibrahim ............ A61N 1/36032 607/57 |
| 2006/0210104 | A1* | 9/2006 | Shennib ................ H04R 25/00 381/315 |
| 2006/0271128 | A1* | 11/2006 | Keuninckx ........ A61N 1/36032 607/60 |
| 2010/0046778 | A1 | 2/2010 | Crawford et al. |
| 2010/0218568 | A1 | 9/2010 | Nakanishi et al. |
| 2011/0112607 | A1 | 5/2011 | Zierhofer |
| 2013/0274826 | A1 | 10/2013 | Darley et al. |
| 2014/0012350 | A1 | 1/2014 | Kasic, III et al. |
| 2014/0056452 | A1 | 2/2014 | Moss et al. |
| 2014/0135871 | A1 | 5/2014 | Meskens |

OTHER PUBLICATIONS

International Search Report and Written Opinion of the International Searching Authority for corresponding International Patent Application No. PCT/IB2016/000088 dated Jun. 10, 2016, 14 pgs.

* cited by examiner

*Primary Examiner* — Allen Porter, Jr.
(74) *Attorney, Agent, or Firm* — Merchant & Gould P.C.

(57) ABSTRACT

Operational modes or settings of a totally implantable cochlear implant can be adjusted or changed based on movement of an external element. Sensors in the totally implantable cochlear implant detect one of several positions of the external element as that element is moved near the implant. Depending on the position detected, one of a plurality of operational modes or settings can be selected.

19 Claims, 10 Drawing Sheets

| MODE | MODE NAME | INDUCTION SIGNAL DETECTED? | MAGNET DETECTED AT FIRST MAGNETIC SENSOR? | MAGNET DETECTED AT SECOND MAGNETIC SENSOR? | ACTIVATE WHICH MICROPHONE? | ACTIVATE WHICH SOUND PROCESSOR? | RANGE FOR WIRELESS COMMUNICATION DEVICE? |
|---|---|---|---|---|---|---|---|
| 1 | "INVISIBLE HEARING" | NO | NO | NO | IMPLANTED | IMPLANTED | NONE |
| 2 | "CONVENTIONAL IMPLANT HEARING" | YES | NO | NO | EXTERNAL | EXTERNAL OR IMPLANTED | SHORT |
| 3 | "REMOTE HEARING" | NO | NO | YES | EXTERNAL | EXTERNAL OR IMPLANTED | LONG |
| 4 | "DISABLED" (NO STIMULATION) | NO | YES | NO | NONE | NONE | NONE |

IMPLANTED AUDITORY PROSTHESIS CONTROL BY COMPONENT MOVEMENT

BACKGROUND

Hearing loss, which can be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient (i.e., the inner ear of the recipient) to bypass the mechanisms of the middle and outer ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or the ear canal. Individuals suffering from conductive hearing loss can retain some form of residual hearing because some or all of the hair cells in the cochlea functional normally.

Individuals suffering from conductive hearing loss often receive a conventional hearing aid. Such hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to conventional hearing aids, which rely primarily on the principles of air conduction, certain types of hearing prostheses commonly referred to as bone conduction devices, convert a received sound into vibrations. The vibrations are transferred through the skull to the cochlea causing motion of the perilymph and stimulation of the auditory nerve, which results in the perception of the received sound. Bone conduction devices are suitable to treat a variety of types of hearing loss and can be suitable for individuals who cannot derive sufficient benefit from conventional hearing aids.

SUMMARY

The technologies described herein enable operational modes or settings of a totally implantable cochlear implant to be adjusted or changed based on movement of an external element. Sensors in the totally implantable cochlear implant detect one of several positions of the external element as that element is moved near the implant. Depending on the position detected, one of a plurality of operational modes or settings can be selected.

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

BRIEF DESCRIPTION OF THE DRAWINGS

The same number represents the same element or same type of element in all drawings.

DETAILED DESCRIPTION

Figure 1:
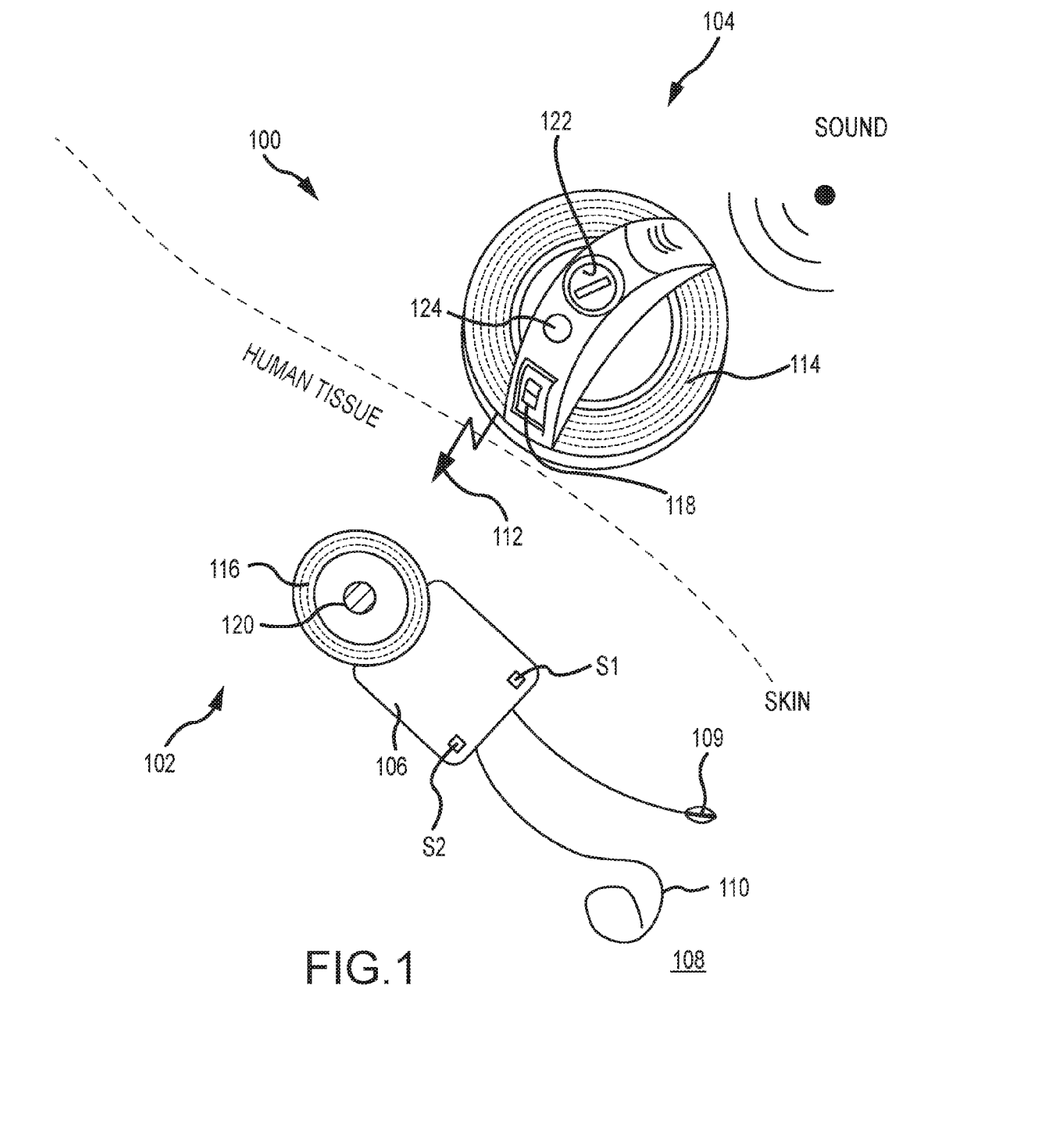
FIG. 1 is a perspective view of an embodiment of an auditory prosthesis, including an implantable portion and an external portion in accordance with one embodiment of the present technology.

FIG. 1 is a perspective view of an embodiment of an auditory prosthesis 100, in this case, a totally implantable cochlear implant. A totally implantable cochlear implant includes an implantable portion 102 and an external portion 104. In general, and as described further herein, the implantable portion 102 of a totally implantable cochlear implant 100 can be used as a standalone auditory prosthesis (e.g., without the need for the external portion 104). However, the external portion 104 can also be utilized in conjunction with the implantable portion 102, and thus operates as a conventional cochlear implant. The implantable portion 102 of the cochlear implant includes a stimulating assembly 106 implanted in a body (specifically, proximate and within the cochlea 108) to deliver electrical stimulation signals to the auditory nerve cells, thereby bypassing absent or defective hair cells. An implantable microphone 109 is connected to the stimulation assembly 106 and allows the implantable portion 102 to be utilized as a standalone auditory prosthesis. An on-board speech processor is contained within the stimulating assembly 106. The speech processor detects external sound via the implantable microphone 109 and converts the detected sound into a signal through a suitable speech processing strategy, which is then sent to the cochlea 108 via one or more electrodes 110. The electrodes 110 of the stimulating assembly 106 differentially activate auditory neurons that normally encode differential pitches of sound. This stimulating assembly 106 enables the brain to perceive a hearing sensation resembling the natural hearing sensation normally delivered to the auditory nerve. The stimulating assembly 106 also includes two magnetic sensors S1, S2, the function of which is described further herein. Additional components of totally implantable cochlear implants are described in FIG. 3 and elsewhere herein.

If the external portion 104 is engaged with the implantable portion 102, the auditory prosthesis 100 functions as a conventional cochlear implant. The external portion 104 can include its own speech processor that detects external sound and converts the detected sound into a coded signal 112 through a suitable speech processing strategy. The coded signal 112 is sent to the implanted stimulating assembly 106 via a transcutaneous link. In an alternative embodiment, the detected external sound can be sent as a signal 112 via the transcutaneous link to the speech processor disposed in the implanted stimulating assembly 106. In one embodiment, the signal 112 is sent from a coil 114 located on the external portion 104 to a coil 116 on the implantable portion 102. The stimulating assembly 106 processes the coded signal 112 to generate a series of stimulation sequences which are then applied directly to the auditory nerve via the electrodes 110 positioned within the cochlea 108. The external portion 104 also includes a battery and a control interface 118, which can include one or more buttons, switches, dials, etc. Permanent magnets 120, 122 are located on the implantable portion 102 and the external portion 104, respectively. In the depicted embodiment, the external portion 104 includes a microphone port 124 connected to a microphone that receives sound. The microphone is connected to one or more internal processors that process and convert the sound into stimulation signals that are sent to the implantable portion 102.

Figure 2:
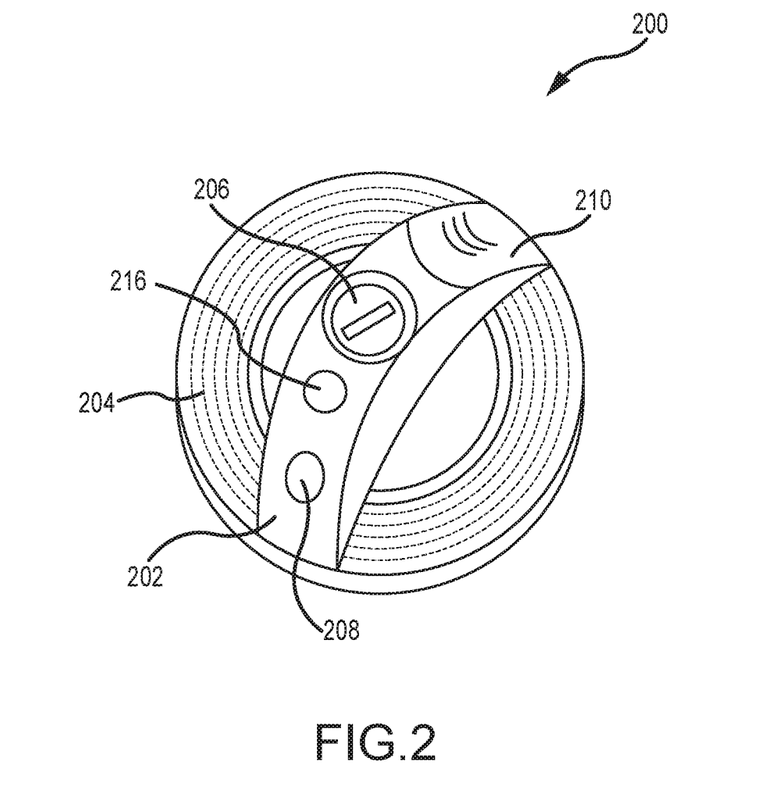
FIG. 2 is a perspective view of an external portion of an auditory prosthesis in accordance with one embodiment of the present technology.

FIG. 2 is a perspective view of an embodiment of an external portion 200 of an auditory prosthesis. The external portion 200 includes a body 202 and a coil 204 connected thereto. The body 202 can include a permanent magnet 206 as described above. The external portion 200 can include a control button 208. A battery door 210 covers a receptacle that includes a battery that can be used to provide recharging power to the implantable portion. A microphone 216 receives sound that is processed by components within the external portion 200, or sent directly to the implantable portion for processing by the speech processor located therein.

Figure 3:
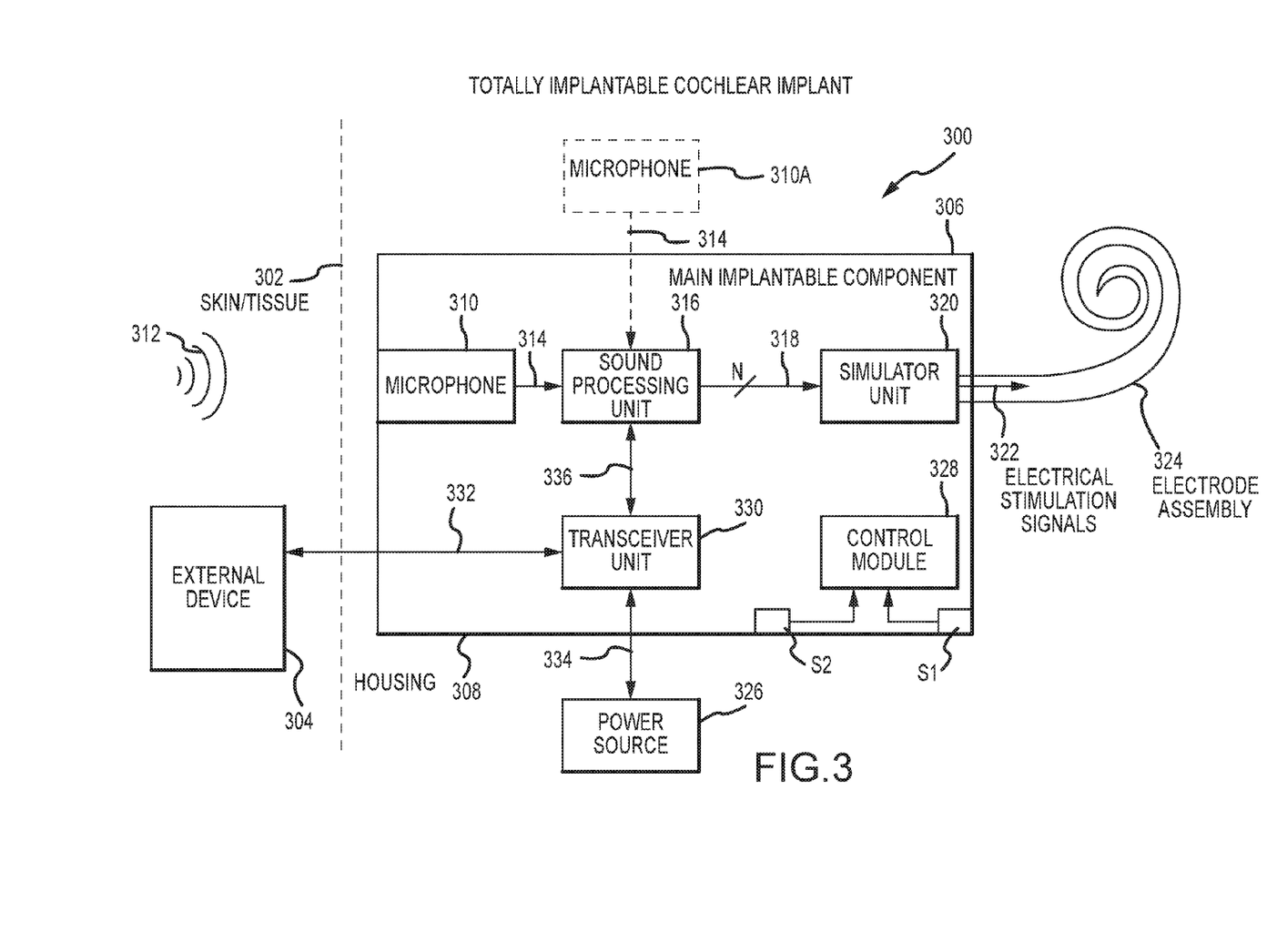
FIG. 3 is a schematic diagram of a totally implantable cochlear implant in accordance with one embodiment of the present technology.

FIG. 3 is a schematic diagram of a totally implantable cochlear implant 300. In a totally implantable cochlear implant 300, all components are configured to be implanted under skin/tissue 302 of a recipient. Because all components of cochlear implant system 300 are implantable, cochlear implant system 300 operates, for at least a finite period of time, without the need of an external device. An external device 304 can be used to charge the internal battery, to supplement the performance of the implanted microphone/system, or for when the internal battery no longer functions. External device 304 can be a dedicated charger or a conventional cochlear implant sound processor.

As noted, cochlear implant system 300 includes a main implantable component 306 having a hermetically sealed, biocompatible housing 308. Disposed in main implantable component 306 is a microphone 310 configured to sense a sound signal 312. Microphone 310 can include one or more components to pre-process the microphone output. As an alternative, the microphone and other aspects of the system can be included in an upgrade or tethered module as opposed to in a unitary body as shown in FIG. 3. For example, a remote microphone 310a tethered to the main implantable component 306 can be utilized.

An electrical signal 314 representing sound signal 312 detected by microphone 310, 310a is provided from the microphone 310, 310a to sound processing unit 316. Sound processing unit 316 implements one or more speech processing and/or coding strategies to convert the pre-processed microphone output into data signals 318 for use by stimulator unit 320. Stimulator unit 320 utilizes data signals 318 to generate electrical stimulation signals 322 for delivery to the cochlea of the recipient. In the example of FIG. 3, cochlear implant system 300 comprises stimulating lead assembly 324 for delivering stimulation signal 322 to the cochlea.

Cochlear implant system 300 also includes a rechargeable power source 326. Power source 326 can comprise, for example, one or more rechargeable batteries. As described below, power is received from an external device, such as external device 304, and is stored in power source 326. The power can then be distributed to the other components of cochlear implant system 300 as needed for operation.

Main implantable component 306 further comprises a control module 328. Control module 328 includes various components for controlling the operation of cochlear implant 300, or for controlling specific components of cochlear implant system 300. For example, controller 328 can control the delivery of power from power source 326 to other components of cochlear implant system 300. For ease of illustration, main implantable component 306 and power source 326 are shown separate. However, power source 326 can alternatively be integrated into a hermetically sealed housing 206 or part of a separate module coupled to component 306. Magnetic sensors S1, S2 are operatively connected to the control module 328 and are described further herein.

As noted above, cochlear implant system 300 further comprises a receiver or transceiver unit 330 that permits cochlear implant system 300 to receive and/or transmit signals 332 to the external device 304. For ease of illustration, cochlear implant system 300 is shown having a transceiver unit 330 in main implantable component 306. In alternative arrangements, cochlear implant system 300 includes a receiver or transceiver unit which is implanted elsewhere in the recipient outside of main implantable component 306.

Transceiver unit 330 is configured to transcutaneously receive power and/or data 332 from external device 304. Power 334 can also be transferred to and from the transceiver unit 330 to charge the power source 326. Signals 336 (power, data, or otherwise) can also be sent to/from the transceiver 330, the sound processing unit 316, and other components of the device as required or desired. As used herein, transceiver unit 330 refers to any collection of one or more implanted components which form part of a transcutaneous energy transfer system. Further, transceiver unit 330 includes any number of component(s) which receive and/or transmit data or power, such as, for example a coil for a magnetic inductive arrangement, an antenna for an alternative RF system, capacitive plates, or any other suitable arrangement. Various types of energy transfer, such as infrared (IR), electromagnetic, capacitive and inductive transfer, can be used to transfer the power and/or data 332 from external device 304 to the main implantable component 306.

As noted, transceiver unit 330 receives power and/or data 332 from external device 304. In the illustrative arrangement of FIG. 3, external device 304 comprises a power source (not shown) disposed in a Behind-The-Ear (BTE) unit. External device 306 also includes components of a transcutaneous energy transfer link formed with transceiver unit 330 to transfer the power and/or data 332 to the main implantable component 306. The external device shown in FIG. 3 is merely illustrative, and other external devices can be alternatively used.

The technologies described herein are directed to changing operational modes of an auditory prosthesis based on the relative position of one component of the prosthesis to another component (e.g., a position of the external portion relative to the implanted position). Each operational mode can include one or more specific device settings. Thus, a change in operational mode can change only one specific setting for the auditory prosthesis, or multiple settings can be changed. In certain embodiments, this can be a temporary position, for example, as the external portion is disengaged from the implantable portion, a detected direction of disengagement will change the operational mode of the auditory prosthesis. The position of the external portion is detected by magnetic or other proximity sensors that are disposed in the implantable portion, as described in more detail below. In the various operational modes, the auditory prosthesis operates based on one or more settings that determine how the auditory prosthesis processes sounds and delivers stimuli to a recipient of the prosthesis. The discrete settings (which also can be adjusted individually in accordance with the disclosures herein) can include activation/deactivation of implanted or external microphones, activation/deactivation of implanted or external sound processors, changes in volume settings, changes in sound processing settings, activation/deactivation of implantable or external power sources, and so on. Any number of settings can be changed or otherwise adjusted based the temporary position of the external portion relative to the implantable portion. For example, disengaging the external portion from the implantable portion in a first direction can cause an increase in stimulation (thus causing a corresponding increase in perceived sound volume), while disengaging the external portion from the implantable portion in a second direction can cause a decrease in stimulation (thus causing a corresponding decrease in perceived sound volume).

Figure 4A:
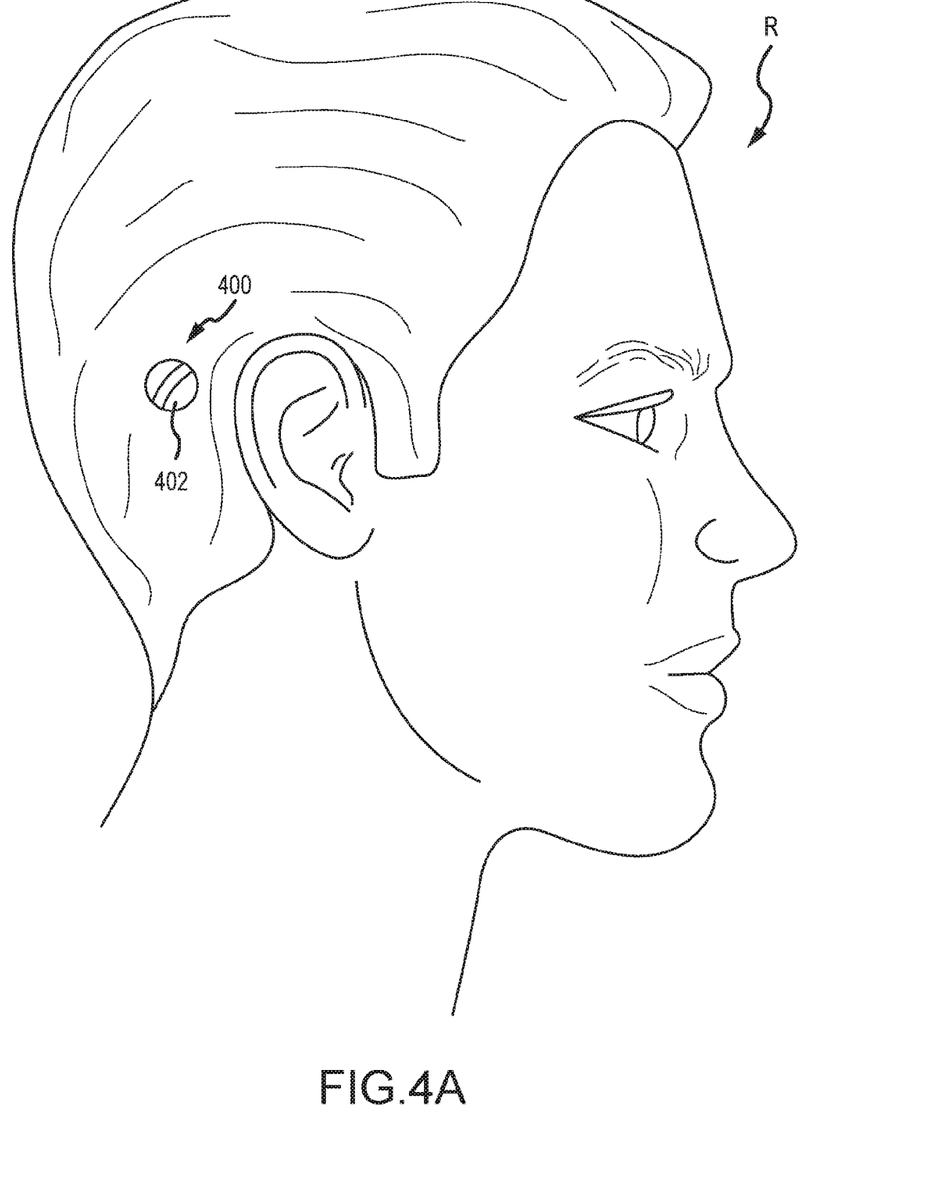
FIGS. 4A and 4B depict a recipient utilizing an auditory prosthesis in a plurality of operational modes in accordance with one embodiment of the present technology.
Figure 4B:
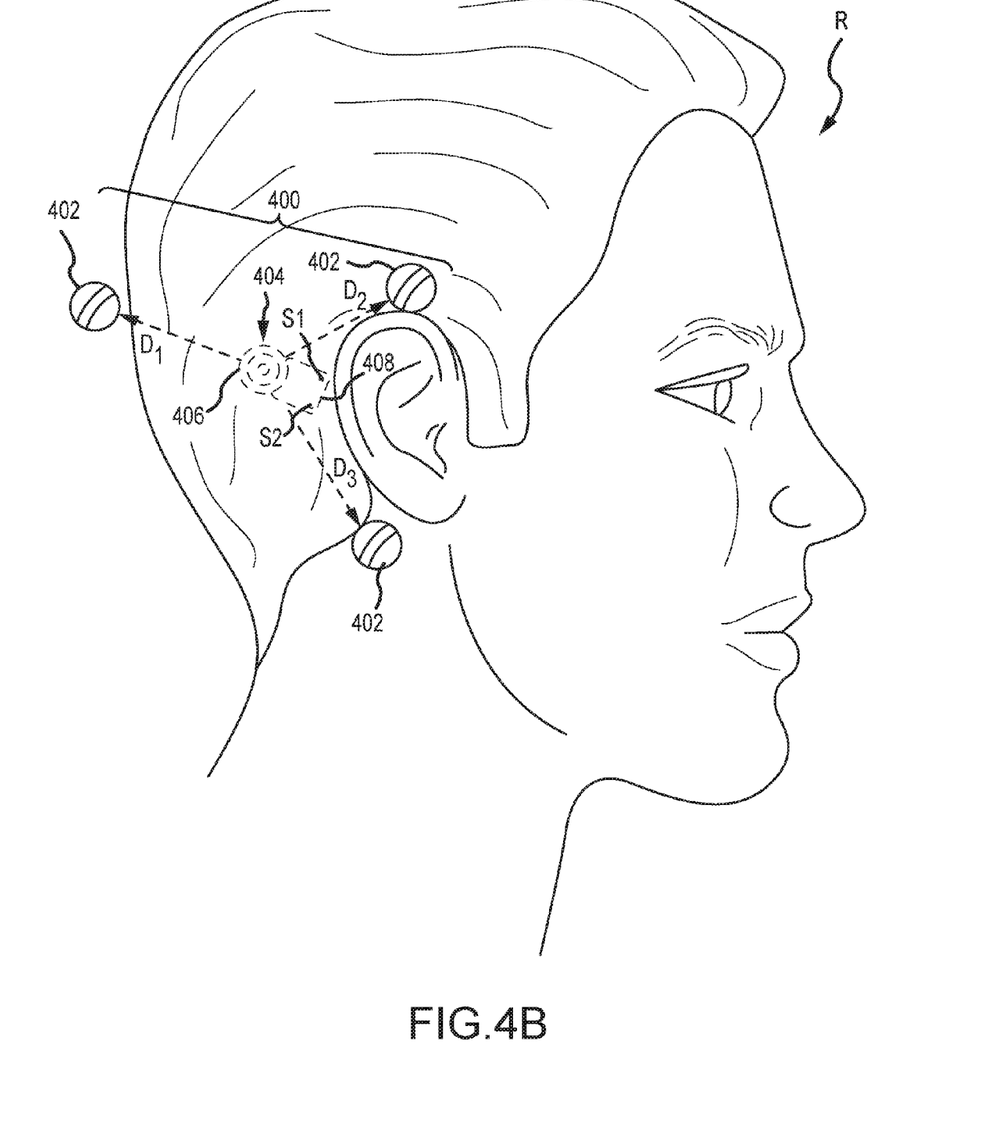

FIGS. 4A and 4B depict a recipient R utilizing an auditory prosthesis 400 in a plurality of operational modes in accordance with one embodiment of the present technology. All components of the auditory prosthesis 400 are not depicted in FIGS. 4A and 4B, for clarity. FIGS. 4A and 4B are described simultaneously. An external portion 402 of the auditory prosthesis 400 is depicted in FIG. 4A as being worn on a head of the recipient R. In FIG. 4A, the engagement between the external portion 402 and an implantable portion 404 (not shown in FIG. 4A) causes the auditory prosthesis 400 to operate in a first operational mode. The engagement of the external portion 402 and the implantable portion 404 can be detected based on signals sent between the induction coils of the respective portions. FIG. 4B depicts the external portion 402 being disengaged with the implantable portion 404 in three discrete directions $D_1$, $D_2$, and $D_3$. The implantable portion 404 includes two sections, a coil section 406 and a stimulation assembly section 408. These two sections, as well as other components of the implantable portion 404, are described above. The stimulation assembly section includes two magnetic sensors S1, S2. As the external portion 402 is disengaged from the implantable portion 404, signals between the respective induction coils cease. As those signals cease, either, both, or none of the magnetic sensors S1, S2 might detect proximity of the magnet disposed in the external portion 402. Proximity signals indicative of such detection can be sent by the magnetic sensors S1, S2 to a control module in the implantable portion 404. If the external portion 402 is moved substantially in the direction $D_1$, neither sensor S1 nor S2 will detect the presence of the external magnet, and the implantable portion 404 of the auditory prosthesis 400 will be set in a second operational mode. If the external portion 402 is moved substantially in the direction $D_2$, sensor S1 will detect the presence of the external magnet, and the implantable portion 404 of the auditory prosthesis 400 will be set in a third operational mode. If the external portion 402 is moved substantially in the direction $D_3$, sensor S2 will detect the presence of the external magnet, and the implantable portion 404 of the auditory prosthesis 400 will be set in a fourth operational mode. The proximity signals are not necessarily binary. That is, depending on the direction of disengagement, both of sensors S1 and S2 can send a proximity signal to the control module. The control module can set the operational mode of the auditory prosthesis based on the higher or lower value or strength of the two proximity signals.

Figure 5:
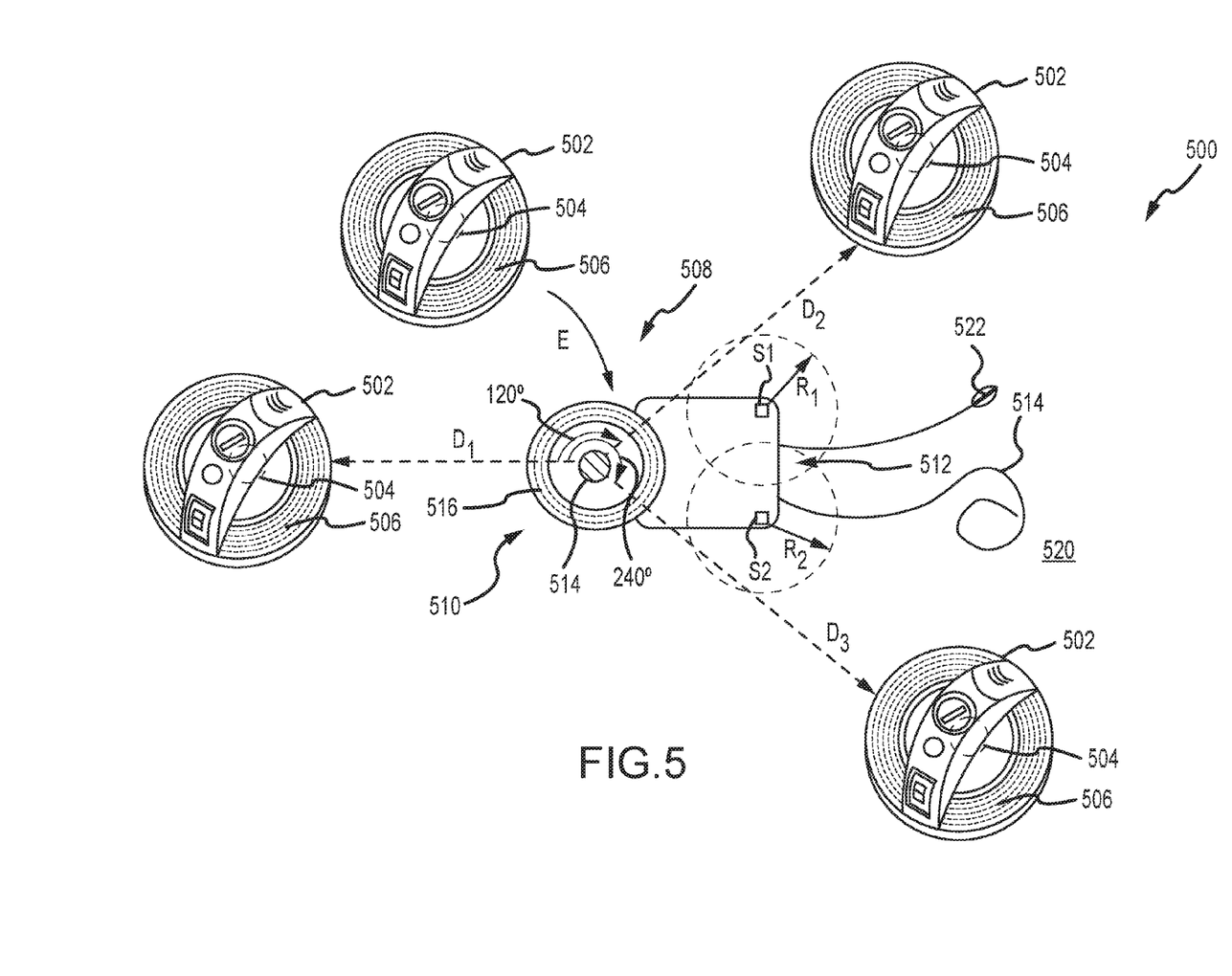
FIG. 5 depicts an implanted auditory prosthesis operating in a plurality of operational modes based on a position of an external portion.

FIG. 5 depicts an implanted auditory prosthesis 500 operating in a plurality of operational modes based on a position of an external portion 502. The external portion 502 includes an external magnet 504 and an external coil 506 implanted therein. The implantable portion 508 includes a coil portion 510 and a stimulation assembly portion 512. The coil portion 510 includes both the implantable magnet 514 and implantable coil 516. The stimulation assembly portion 512 includes magnetic sensors S1, S2 and is connected to the stimulating electrodes 518, which are disposed, once implanted, in the cochlea 520. An implantable microphone 522 discrete from the stimulation assembly portion 512 is also connected to the stimulation assembly portion 512.

An operational mode of the auditory prosthesis 500 is, again, based on the position of the external portion 502, relative to the implantable portion 508 as those two portions are disengaged. When the external portion 504 is engaged E with the implantable portion 508, signals between the coils 506, 516 are detected, and one operational mode is set. Removing the external portion 504 from the implantable portion 508 in one of directions $D_1$, $D_2$, and $D_3$ sets the auditory prosthesis 500 in one of three other operational modes, depending on the proximity of the external magnet 504 to either, both, or none of the magnetic sensors S1, S2. As can be seen in FIG. 5, each of the magnetic sensors S1, S2 has a detection radius $R_1$, $R_2$, respectively. In the depicted embodiment, the two detection radii $R_1$, $R_2$ overlap, but do not extend so far as to overlap the other sensor. As the external magnet 504 passes through either detection radius $R_1$, $R_2$, the associated sensor sends a proximity signal to the control module so as to set or change a different operational mode or setting of the auditory prosthesis 500. Should the external magnet 504 be removed so as to pass through both detection radii $R_1$, $R_2$, the values of each proximity signal sent to the control module will be measured. The higher (or lower) value will then be utilized to determine the operational mode set for the auditory prosthesis 500. Disengagement of the enteral portion 504 with the implantable portion 508, without detection by either sensor S1, S2 will also change the operational mode. The directions $D_1$, $D_2$, and $D_3$ are note depicted absolute, defined directions based on a specific angle. The directions $D_1$, $D_2$, and $D_3$ are merely general depictions of disengagement directions that can be utilized to change operational modes. The directions can vary based on the length of the detection radii of each sensor, number of sensors, location of each sensor on the stimulation assembly, etc. In one embodiment, direction $D_1$ is disposed approximately at 0°, direction $D_2$ is disposed at approximately 120° from direction, and direction $D_3$ is disposed at approximately 240° from direction $D_1$; however, other angles are contemplated. In other embodiments, operational modes can also be changed based on the direction in which the external portion 502 is engaged with the implantable portion 508. For example, if one of the sensors S1, S2 detects the presence of the magnet 504, followed shortly thereafter by detection of induction coil 506, 516 signals, a different operational mode can be set.

Figure 6:
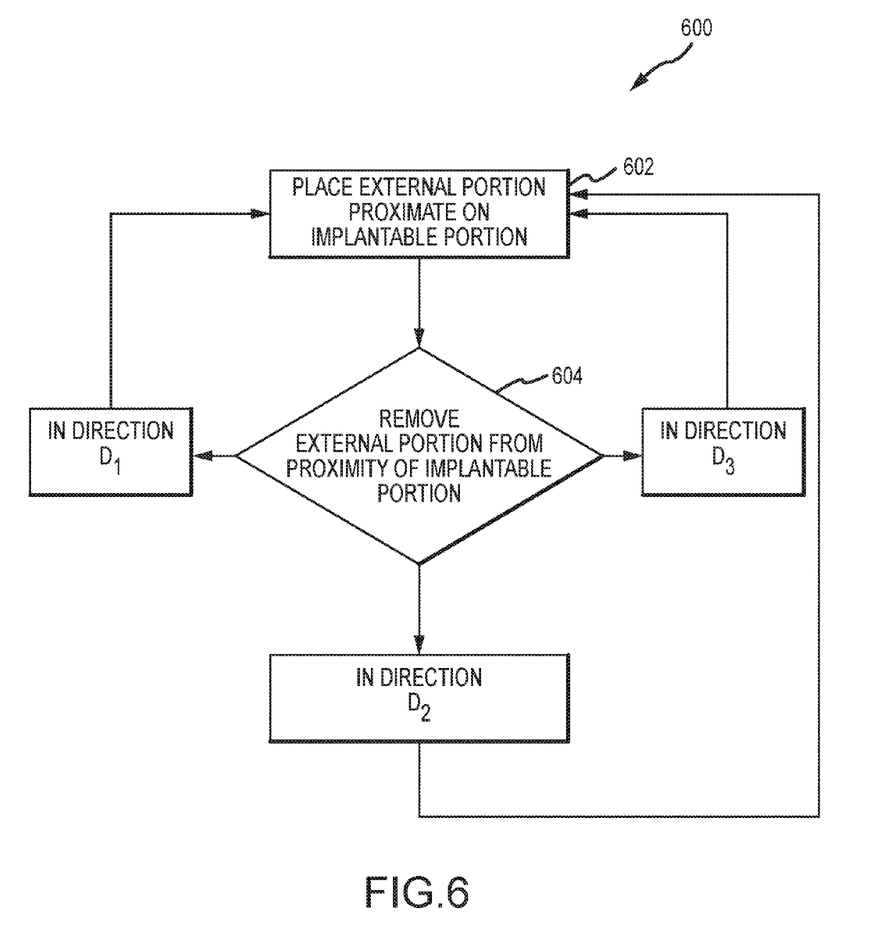
FIG. 6 depicts a method of changing operational settings for an auditory prosthesis in accordance with one embodiment of the present technology.

FIG. 6 depicts a method 600 of changing operational settings for an auditory prosthesis in accordance with one embodiment of the present disclosure. The auditory prosthesis includes an implantable portion and an external portion. The external portion can be, in certain embodiments, the external portion of a conventional cochlear implant (e.g., including a microphone, sound processing software, control buttons, etc.) or it can be a more basic device (e.g., nothing more than a magnet, the position thereof dictating an operational setting of the device). In another embodiment, the external portion can be a battery-charging element (utilizing either or both of a battery or plug-in power source), which can be used to charge the implanted power source on the implantable portion of the auditory prosthesis. The method 600 begins at operation 602, where the external portion is placed by the recipient proximate the implantable portion. Proximity of the external portion and implantable portion can be confirmed by detecting signals transmitted between the induction coils contained in each portion, or detecting a change in the magnetic field generated by the mating magnets. When engaged, the auditory prosthesis operates in a first operational mode. When the recipient wishes to change the operational mode for her device, decision operation 604, they can disengage or remove the external portion from the implantable portion. Disengagement in either of direction $D_1$, $D_2$, or $D_3$ will result in a change in the operational mode. Thereafter, the recipient can place the external portion back in proximity to the implantable portion, operation 602, thereby placing the auditory prosthesis back in the first operational mode. While the method 600 is depicted as identifying disengagement in three different directions (e.g., direction $D_1$, $D_2$, or $D_3$), in alternate embodiments, the method 600 can identify more or fewer directions and/or operational modes.

Figure 7:
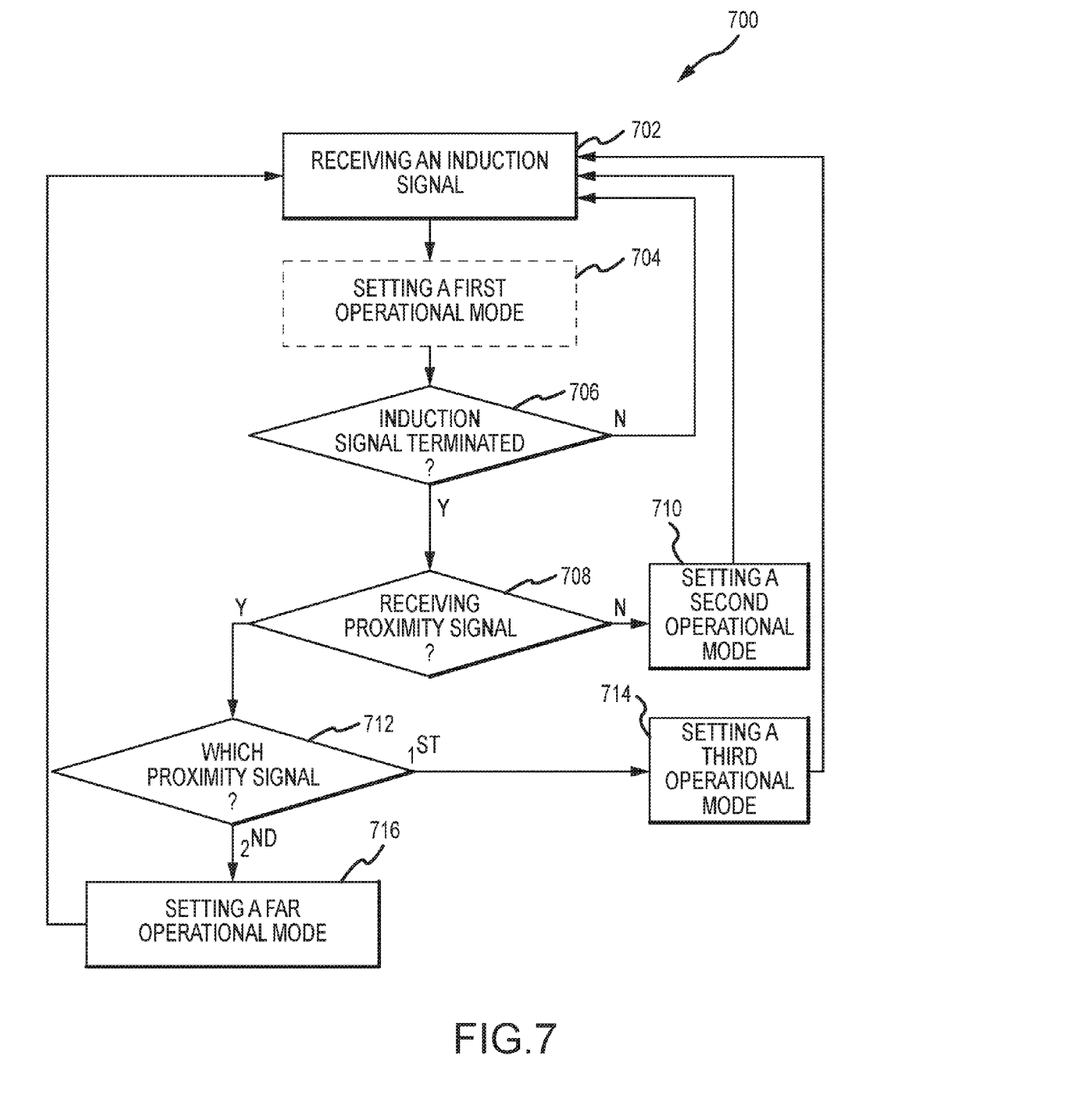
FIG. 7 depicts a method of changing operational settings for an auditory prosthesis in accordance with another embodiment of the present technology.

FIG. 7 depicts a method 700 of changing operational settings for an auditory prosthesis in accordance with another embodiment of the present technology. The method 700 begins at operation 702, where an induction signal from an external coil is received at an implantable portion of an auditory prosthesis. Thereafter, the auditory prosthesis can be set in a first operational mode, operation 704, but this is not required. If the induction signal is not terminated, operation 706, flow branches NO and the auditory prosthesis remains in the operational mode previously set. If the induction signal is terminated, flow branches YES to determination operation 708, where receipt of a proximity signal is determined. If no such proximity signal is received, flow branches NO to operation 710, where a second operational mode is set. Flow can return to operation 702 if an induction signal is once again received. If a proximity signal is received, flow branches YES to determination operation 712, where the particular proximity signal is identified. If the proximity signal was received from a first proximity sensor, flow branches to operation 714, where a third operational mode is set. Flow can return to operation 702 if an induction signal is once again received. If the proximity signal was received from a second proximity sensor, flow branches to operation 716, where a fourth operational mode is set. Flow can return to operation 702 if an induction signal is once again received. Proximity signals sent from more proximity signals can also be accommodated as described elsewhere herein.

In general, the embodiments described herein include proximity sensors disposed on an implantable portion of an auditory prosthesis. In alternative embodiments, however, proximity sensors can be disposed on an external portion. Since a magnet is present in the implantable portion as well as the external portion, proximity sensors in the external portion can detect the position of the implanted magnet and the operational mode of the auditory prosthesis can be changed based on this detection. Auditory prostheses that utilize proximity sensors on both the implantable portion and the external portion are also contemplated.

EXAMPLE

Figure 8:
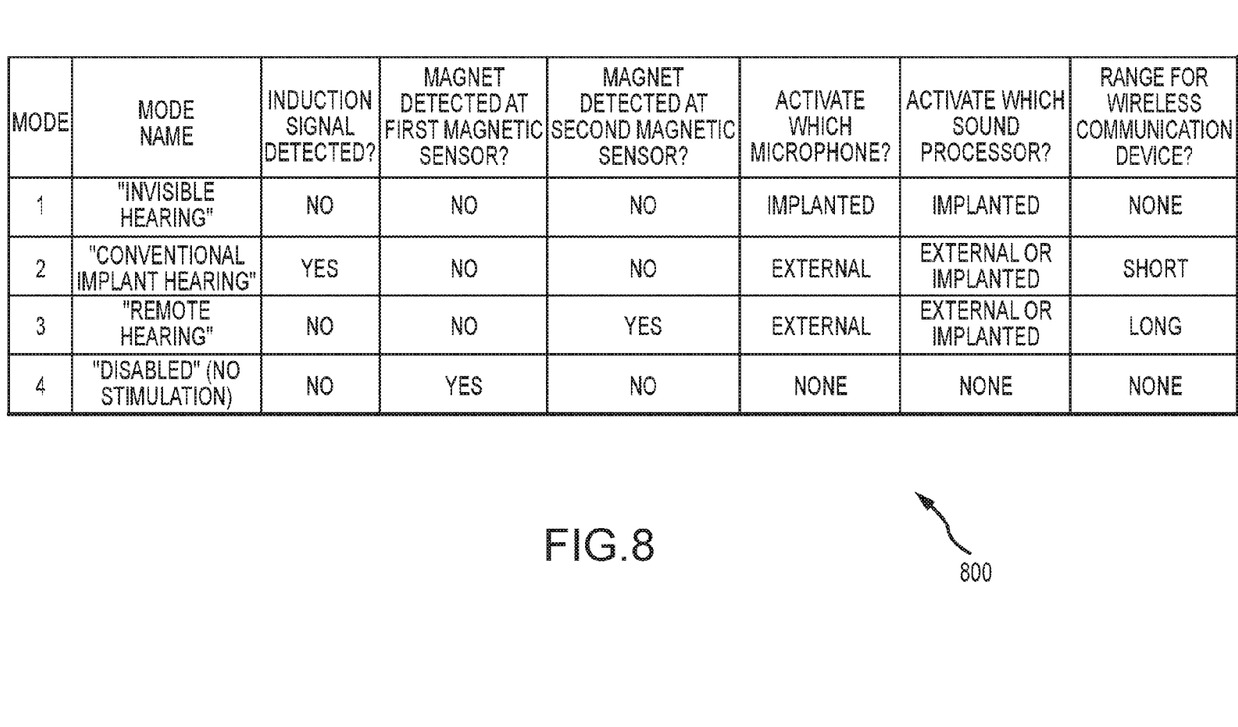
FIG. 8 depicts a matrix of operational settings for an auditory prosthesis in accordance with one embodiment of the present technology.

FIG. 8 depicts a matrix 800 of operational modes (each having a plurality of component settings) for an auditory prosthesis in accordance with one embodiment of the present technology. The matrix 800 depicts but one embodiment of the various operational modes that can be developed utilizing the disclosures herein. Other operational modes are contemplated. The auditory prosthesis of the Example depicted in FIG. 8 has the following characteristics. The auditory prosthesis is a totally implanted cochlear implant and includes implantable portion and an external portion. Relevant to this Example, the implantable portion has an implantable induction coil, a first magnetic sensor, and a second magnetic sensor. The implantable portion also has an implantable microphone, an implantable sound processor, and a wireless communication device having a plurality of range settings (e.g., an induction coil that can alter its signal so as to allow communication over short or long distances), which enables it to communicate with the external portion. The external portion has an external induction coil and a permanent magnet. The external portion also has an external microphone, an external sound processor, and an induction coil that can alter its signal based on distance, again, as described above, which enables it to communicate with the implantable portion. Configurations of such embodiments of auditory prostheses are depicted herein.

The mode numbers (1-4) and mode names are utilized for convenience of the reader to distinguish between the various modes and should not be considered limiting. In alternative embodiments of the present Example, the mode numbers should not be considered mutually exclusive to the named mode. That is, mode 3 need not be considered the "Remote Hearing" mode. In the depicted Example, if the induction signal is not detected and the proximity of the magnet to either of the two magnetic sensors is not detected, this means the external portion is not proximate the implantable portion. Accordingly, the auditory prosthesis operates as a totally implantable cochlear implant. In this "Invisible Hearing" mode, the implanted microphone is activated, along with the implanted sound processor. The wireless communication device is deactivated, since the implantable portion need not communicate with the external portion in this mode.

If the induction signal is detected and the proximity of the magnet to either of the two magnetic sensors is not detected, this means the external portion is engaged with the implantable portion. Accordingly, the auditory prosthesis operates as a conventional cochlear implant. In this "Conventional Implant Hearing" mode, the external microphone is activated, and the wireless communication device is set for short range communication so as to send signals between the implantable portion and the external portion. Either of the implanted or external sound processor can be activated. For example, if the battery life on the implanted device is low, the external sound processor can be operational so as not to further tax battery life.

If the induction signal is not detected and the magnet is detected proximate the second magnetic sensor, this means the external portion has been removed from the proximity of the implantable portion in a particular direction. Accordingly, the auditory prosthesis operates in a "Remote Hearing" mode. In this mode, the external microphone is activated, and the wireless communication device is set for long-range communication between the implantable portion and the external portion. Such a mode is valuable when the recipient is sleeping, for example. The recipient is able keep her external portion nearby (on a bedside charging station, e.g.). Any sounds emitted at night (a smoke detector, for example) will be sent as stimuli to the implantable portion. Either of the implanted or external sound processor can be activated. For example, if the battery life on the implanted device is low, the external sound processor can be operational so as not to further tax battery life.

If the induction signal is not detected and the magnet is detected proximate the first magnetic sensor, this means the external portion has been removed from the proximity of the implantable portion in a different direction. Accordingly, the auditory prosthesis is placed in a "Disabled" mode. In this mode, the auditory prosthesis is entirely inoperable.

Figure 9:
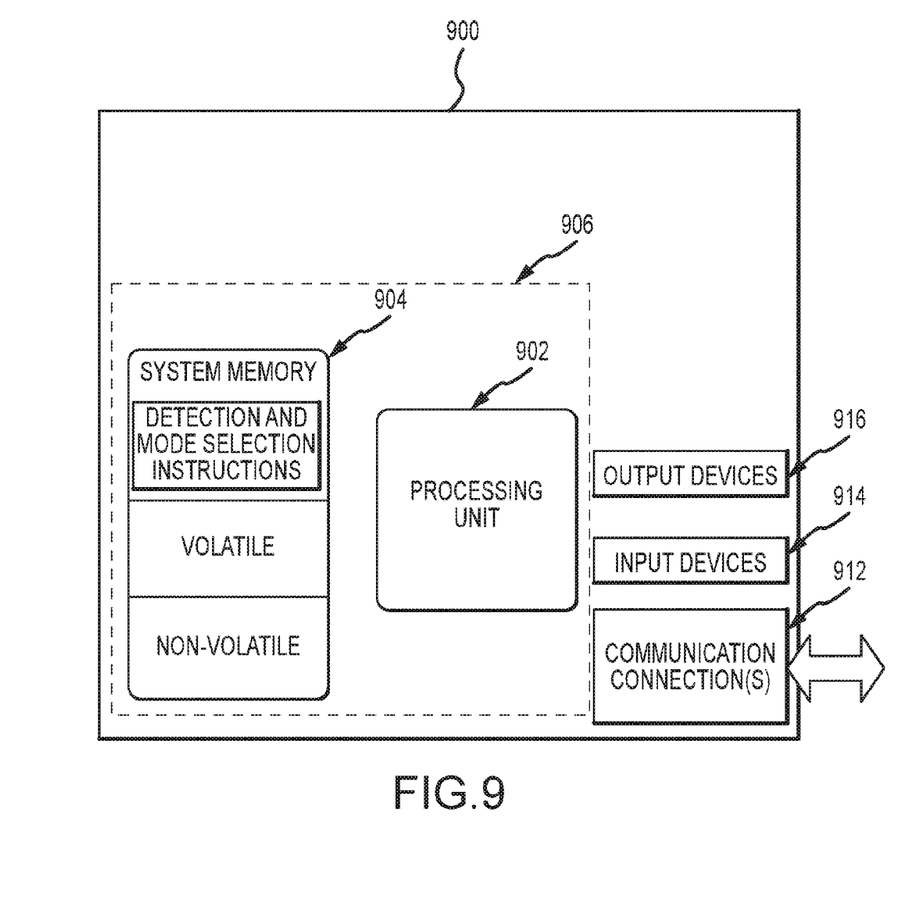
FIG. 9 illustrates one example of a suitable operating environment in which one or more of the present examples can be implemented.

FIG. 9 illustrates one example of a suitable operating environment 900 in which one or more of the present embodiments can be implemented. This is only one example of a suitable operating environment and is not intended to suggest any limitation as to the scope of use or functionality. Other well-known computing systems, environments, and/or configurations that can be suitable for use include, but are not limited to, auditory prostheses. In embodiments, an auditory prosthesis includes a processing unit and memory, such as processing unit 906 and memory 904. As such, the basic configuration 906 is part of an auditory prosthesis and/or another device working in conjunction with the auditory prosthesis.

In its most basic configuration, operating environment 900 typically includes at least one processing unit 902 and memory 904. Depending on the exact configuration and type of computing device, memory 904 (storing, among other things, instructions to implement and/or perform methods, operational mode changes, and other functionality disclosed herein) can be volatile (such as RAM), non-volatile (such as ROM, flash memory, etc.), or some combination of the two. This most basic configuration is illustrated in FIG. 9 by dashed line 906. Similarly, environment 900 can also have input device(s) 914 such as a microphone, physical inputs (e.g., buttons), vibration sensors, etc. Other exemplary input device(s) include, but are not limited to, touch screens or elements, dials, switches, voice input, etc. and/or output device(s) 916 such as speakers, stimulation assemblies, etc. Also included in the environment can be one or more communication connections, 912, such as LAN, WAN, point to point, Bluetooth, RF, etc.

Operating environment 900 typically includes at least some form of computer readable media. Computer readable media can be any available media that can be accessed by processing unit 902 or other devices comprising the operating environment. By way of example, and not limitation, computer readable media can comprise computer storage media and communication media. Computer storage media includes volatile and nonvolatile, removable and non-removable media implemented in any method or technology for storage of information such as computer readable instructions, data structures, program modules or other data. Computer storage media includes RAM, ROM, EEPROM, flash memory or other memory technology, solid state storage, or any other tangible or non-transitory medium which can be used to store the desired information. Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 900 can be a single device operating in a networked environment using logical connections to one or more remote devices. The remote device can be an auditory prosthesis, a personal computer, a server, a router, a network PC, a peer device or other common network node, and typically includes many or all of the elements described above as well as others not so mentioned. The logical connections can include any method supported by available communications media. Such networking environments are commonplace in offices, enterprise-wide computer networks, intranets and the Internet.

In some embodiments, the components described herein comprise such modules or instructions executable by operating environment 900 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some embodiments, computer system 900 is part of a network that stores data in remote storage media for use by the computer system 900.

The embodiments described herein can be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices can be employed to perform the functionality disclosed herein without departing from the scope of the disclosure.

This disclosure described some embodiments of the present technology with reference to the accompanying drawings, in which only some of the possible embodiments were shown. Other aspects can, however, be embodied in many different forms and should not be construed as limited to the embodiments set forth herein. Rather, these embodiments were provided so that this disclosure was thorough and complete and fully conveyed the scope of the possible embodiments to those skilled in the art.

Although specific embodiments were described herein, the scope of the technology is not limited to those specific embodiments. One skilled in the art will recognize other embodiments or improvements that are within the scope of the present technology. Therefore, the specific structure, acts, or media are disclosed only as illustrative embodiments. The scope of the technology is defined by the following claims and any equivalents therein.

What is claimed is:

1. An apparatus comprising:
an implantable auditory prosthesis comprising an implantable magnet and a first proximity sensor, wherein the implantable auditory prosthesis comprises a first operational mode and a second operational mode; and
an external control element configured to communicate with the implantable auditory prosthesis, wherein the external control element comprises an external magnet, and wherein the implantable auditory prosthesis operates in the first operational mode when the external magnet is engaged with the implantable magnet, and wherein the implantable auditory prosthesis operates in the second operational mode when the external magnet is disengaged from the implantable magnet and the first proximity sensor detects a presence of the external magnet,
wherein the implantable auditory prosthesis further comprises a second proximity sensor, and wherein the presence of the external magnet is characterized by a first signal received at the first proximity sensor being stronger than a second signal received at the second proximity sensor.

2. The apparatus of claim 1, wherein the implantable auditory prosthesis further comprises a third operational mode, wherein the implantable auditory prosthesis operates in the third operational mode when the external magnet is disengaged from the implantable magnet and the first proximity sensor fails to detect the presence of the external magnet.

3. The apparatus of claim 2, wherein the implantable auditory prosthesis further comprises a disabled mode, wherein the implantable auditory prosthesis enters the disabled mode when the external magnet is disengaged from the implantable magnet and the second proximity sensor detects the presence of the external magnet.

4. The apparatus of claim 3, wherein the implantable auditory prosthesis comprises an implantable microphone and the external control element comprises an external microphone, and wherein when in the disabled mode, both of the implantable microphone and the external microphone are disabled.

5. The apparatus of claim 2, wherein the implantable auditory prosthesis comprises an implantable microphone and the external control element comprises an external microphone, and wherein when in the third operational mode, the implantable microphone is enabled and the external microphone is disabled.

6. The apparatus of claim 5, wherein when in the third operational mode, a control signal is received by the implantable auditory prosthesis from the external control element.

7. The apparatus of claim 1, wherein the implantable auditory prosthesis comprises an implantable microphone and the external control element comprises an external microphone, and wherein when in the first operational mode, the implantable microphone is disabled and the external microphone is enabled and the external control element sends signals to the implantable auditory prosthesis via an inductive link.

8. The apparatus of claim 7, wherein when in the second operational mode, the implantable microphone is disabled and the external microphone is enabled and the external control element sends signals to the implantable auditory prosthesis via a wireless link.

9. An apparatus comprising:
an external control element comprising:
an external magnet; and
an implantable auditory prosthesis comprising:
a processor;
an implantable magnet; and
first and second magnetic sensors in communication with the processor,
wherein the processor selects a first operational mode when the external magnet is engaged with the implantable magnet;
wherein the processor selects a second operational mode when the external magnet is disengaged from the implantable magnet and the first magnetic sensor detects a presence of the external magnet; and
wherein the presence of the external magnet is characterized by a first signal received at the first magnetic sensor being stronger than a second signal received at the second magnetic sensor.

10. The apparatus of claim 9, wherein:
the external control element comprises an external microphone;
the implantable auditory prosthesis comprises an implantable microphone in communication with the processor; and
the processor sends an activation signal to activate at least one of the external microphone and the implantable microphone based at least in part on the selected operational mode.

11. The apparatus of claim 9, wherein a position signal is received from the at least one of the first and second magnetic sensors.

12. The apparatus of claim 9, wherein the external control element comprises an external communication coil and a position signal is received from the external communication coil.

13. The apparatus of claim 9, wherein a position signal is received when the external magnet is aligned with the implantable magnet.

14. A medical device comprising:
an external component comprising an external magnet; and
an implantable component, wherein the implantable component comprises:
an implantable magnet;
a first magnet sensor,
a second magnet sensor, wherein the second magnet sensor is spaced from the first magnet sensor, and
a processor connected to the first magnet sensor and the second magnet sensor,
wherein the processor is configured to select a first operational mode when the external magnet is disengaged with the implantable magnet;
wherein the processor is configured to select a second operational mode when the external magnet is disengaged from the implantable magnet and the first magnet sensor detects a presence of the external magnet; and
wherein the presence of the external magnet is characterized by a first signal received at the first magnet sensor being stronger than a second signal received at the second magnet sensor.

15. The medical device of claim 14, wherein the processor is configured to enter a disabled mode based at least in part on: a relative strength of the first signal and the second signal, and an absence of power or data being received from the external component.

16. The medical device of claim 14, wherein at least one of the first and second magnet sensors comprises an induction coil, and wherein the induction coil is configured to receive power or data from the external component.

17. The medical device of claim 14, wherein a relative strength of the first signal and the second signal is indicative of a direction of movement of the external component relative to the implantable component.

18. The medical device of claim 14, wherein the processor is configured to determine a position signal based on a relative strength of the first signal and the second signal, and determine a direction of movement of the external component based on changes in the position signal.

19. The medical device of claim 14, wherein the medical device is a hearing prosthesis selected from the group consisting of: a cochlear implant, an active bone conduction device, and a middle ear implant.

* * * * *